United States Patent [19]

Tehim et al.

[11] Patent Number: 5,674,877
[45] Date of Patent: Oct. 7, 1997

[54] MUSCARINIC RECEPTOR LIGANDS

[75] Inventors: Ashok Tehim; Sumanas Rakhit, both of Mississauga, Canada

[73] Assignee: Allelix Biopharmaceuticals Inc., Ontario, Canada

[21] Appl. No.: 637,181

[22] Filed: Apr. 24, 1996

Related U.S. Application Data

[62] Division of Ser. No. 358,471, Dec. 19, 1994, Pat. No. 5,561,127.
[51] Int. Cl.$^6$ .................... A61K 31/49; C07D 471/08; C07D 487/08
[52] U.S. Cl. .................... 514/300; 514/414; 546/122; 548/453
[58] Field of Search .................... 548/453; 546/122; 514/300, 414

[56] References Cited

U.S. PATENT DOCUMENTS

| | | | |
|---|---|---|---|
| 3,539,573 | 11/1970 | Schmutz et al. | 260/268 |
| 3,546,226 | 12/1970 | Schmutz et al. | 260/268 |
| 3,751,415 | 8/1973 | Schmutz et al. | 260/268 |
| 3,758,479 | 9/1973 | Schmutz et al. | 260/268 |
| 3,908,010 | 9/1975 | Schmutz et al. | 424/250 |
| 3,983,234 | 9/1976 | Sayers | 424/250 |
| 4,096,261 | 6/1978 | Horrom et al. | 424/250 |
| 5,006,522 | 4/1991 | Engel et al. | 514/221 |
| 5,354,747 | 10/1994 | Hansen, Jr. et al. | 514/211 |

FOREIGN PATENT DOCUMENTS

| | | | |
|---|---|---|---|
| 772160 | 11/1967 | Canada | 260/239.11 |
| WO 93/20819 | 10/1993 | WIPO | A61K 31/445 |

OTHER PUBLICATIONS

Bloom et al., J. Pharmacology and Experimental Therapeutics, 1987, 240(1):51 "Characterization of High Affinity [$^3$H]Pienzepine and (−)-[$^3$H]Quinuclidinyl Benzilate Binding to Muscarinic Cholinergic Receptors in Rabbit Peripheral Lung".
Clark et al., J. Med. Chem., 1993, 36:2645 "2–(Quinuclidin–3–yl)pyrido[4,3–b ]indol–1–ones and Isoquinolin–1–ones. Potent Conformationally Restricted 5–HT$_3$ Receptor Antagonists".
Giani et al. Synthesis, 1985, p. 550 "A New Facile Synthesis of 11–Oxo–10,11–dihydro–5H–dibenzo[b,e][1,4]diazepines".
Harden et al. TIPS, Feb. 1986 Supplement "Characteristics of two biochemical responses to stimulation of muscarinic cholinergic receptors".
Harris et al. J. Med. Chem., 1982, 25:855 "Affinity of 10–(4–Methylpiperazino)dibenz[b,f]oxepins for Clozapine and Spiroperidol Binding Sites in Rat Brain".
Jaen et al. Annual Reports in Medicinal Chemistry–29, p. 23 "Recent Advances in the Design and Characterization of Muscarinic Agonists and Antagonists".
Jones et al. Life Sciences, 1993, 52:457 "Muscarinic Receptor Subtypes: Modulation of Ion Channels".
Kaiser et al. Neurotransmissions, 1987, vol. III, No. 2 "Cholinergic Agents".
Klunder et al. J. Med. Chem., 1992, 35:1887 "Novel Non–Nucleoside Inhibitors of HIV–1 Reverse Transcriptase. 2. Tricyclic Pyridobenzoxazepinones and Dibenzoxazepinones".
dePaulis et al. J. Med. Chem., 1981, 24(9):1021 "Synthesis of Clozapine Analogues and Their Affinity for Clozapine and Spiroperidol Binding Sites in Rat Brain".
Sindelair et al. Coll. Czechoslov. Chem. Commun., 1977, 42:2231 "noncataleptic Potential Neuroleptics: 2–Nitro and 2–Hydroxy derivatives of 10–(4–Methylpiperazino)–10, 11–Dihydrodibenzo[b,f]Thiepin".
Watson et al. Trends Pharmacol. Sci., Suppl. 7, 1986, p. 46 "Biochemical and functional basis of putative muscarinic receptor subtypes and its implications".

*Primary Examiner*—Philip I. Datlow
*Attorney, Agent, or Firm*—Nikaido, Marmelstein, Murray & Oram LLP

[57] ABSTRACT

Described herein are D4 receptor-selective compounds of the general formula I:

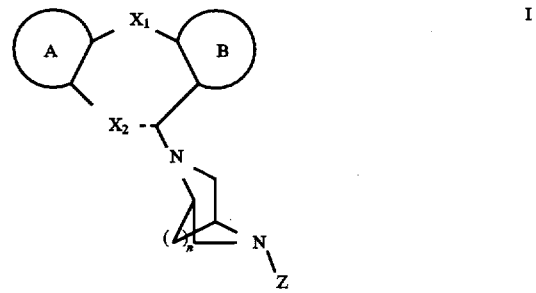

wherein:

A and B are independently selected, optionally substituted, saturated or unsaturated 5- or 6-membered, homo- or heterocyclic rings;
$X_1$ is selected from $CH_2$, O, NH, S, C=O, CH—OH, CH—NEt$_2$, C=CHCl, C=CHCN, N—C$_{1-4}$alkyl, N-acetyl, SO$_2$ and SO;
$X_2$ - - - is selected from N=, CH$_2$—, CH=, C(O)—, O—, and S—;
n is 1 or 2; and
Z is selected from C$_{1-6}$alkyl optionally substituted with a substituent selected from OH, halo, C$_{1-4}$alkyl and C$_{1-4}$alkoxy;
and acid addition salts, solvates and hydrates thereof. Their use as ligands for dopamine receptor identification and in a drug screening program, and as pharmaceuticals to treat indications in which the M1/M2 receptor is implicated, such as schizophrenia, is also described.

9 Claims, No Drawings

MUSCARINIC RECEPTOR LIGANDS

This is a division of application Ser. No. 08/358,471, filed Dec. 19, 1994 now U.S. Pat. No. 5,561,127.

BACKGROUND TO THE INVENTION

Among the neuronal and peripheral cell receptors that bind the neurotransmitter acetylcholine (ACh), are the muscarinic receptors. There are reportedly five subtypes classified as M1 through M5, of which the M1 and M2 have been implicated in the etiology of such medical conditions as Parkinson's disease, cardiac disorders and gastrointestinal disorders. It has been suggested that compounds capable of interfering with the action of acetylcholine at these receptors, would be useful to treat these conditions. However, the tendency for ligands to bind indiscriminately to various other receptor types, such as serotonin and dopamine receptors has made difficult the development of drugs that are muscarinic M1/M2 receptor-selective. It would nevertheless be desirable to provide such a compound, particularly so that side effects are minimized during treatment of the conditions noted above.

It is an object of the present invention to provied a compound having muscarinic M1/M2 receptor affinity.

It is an object of the present invention to provide a compound having an improved muscarinic M1/M2 receptor selectivity profile.

It is a further object of the present invention to provide a pharmaceutical composition comprising a compound of the present invention, as active ingredient.

SUMMARY OF THE INVENTION

According to one aspect of the present invention, there is provided a compound of
Formula I:

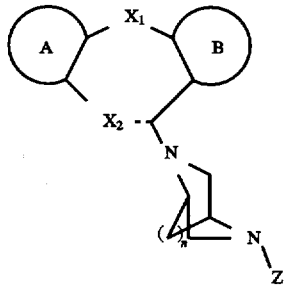

wherein
A and B are independently selected, optionally substituted, saturated or unsaturated 5- or 6-membered, homo- or heterocyclic rings;
$X_1$ is selected from $CH_2$, O, NH, S, C=O, CH—OH, CH—$NEt_2$, C=CHCl, C=CHCN, N—$C_{1-4}$alkyl, N-acetyl, $SO_2$ and SO;
$X_2$ - - - is selected from N=, $CH_2$—, CH=, C(O)—, O—, and S—;
n is 1 or 2; and
Z is selected from $C_{1-6}$alkyl optionally substituted with a substituent selected from OH, halo, $C_{1-4}$alkyl and $C_{1-4}$alkoxy;
and acid addition salts, solvates and hydrates thereof.

According to another aspect of the invention, there is provided a pharmaceutical composition comprising a compound of Formula I and a pharmaceutically acceptable carrier.

In a further aspect of the invention, there is provided an analytical method in which a compound of the invention is used to distinguish muscarinic M1/M2 receptors from serotonin receptors such as 5-HT2 and/or from dopamine receptors such as the D2 and D4 sub-types.

These and other aspects of the present invention are now described in greater detail hereinbelow.

DETAILED DESCRIPTION AND PREFERRED EMBODIMENTS

The invention relates to compounds that bind the muscarinic M1/M2 receptor in a selective manner, relative to serotonin 5-HT2 and/or dopamine D2 and D4 receptors. In accordance with one of its aspects, the present invention accordingly provides compounds that conform to Formula I:

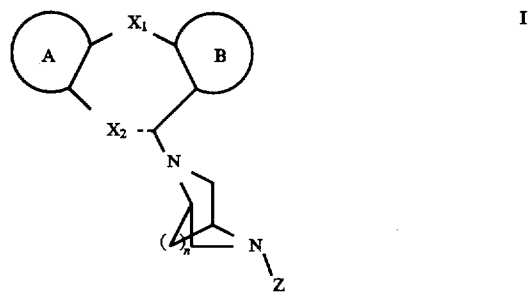

In embodiments of the invention, Z is selected from $C_{1-6}$alkyl optionally substituted with a substituent selected from OH, halo, $C_{1-4}$alkyl, $C_{1-4}$alkoxy and aryl. Particular embodiments of the invention include those in which Z is $C_{1-6}$alkyl such as methyl, ethyl, linear or branched propyl, butyl, pentyl and hexyl optionally substituted with an aryl substituent such as phenyl. More particularly Z is selected from methyl or benzyl. Most particularly, Z is methyl. In other embodiments of the invention, n is 1 corresponding to the diazabicyclo(2.2.1)heptane ring or n is 2 corresponding to the diazabicyclo(2.2.2)octane ring. In a particular embodiment n is 1.

The tricyclic function to which the diazabicycloheptane ring is coupled can have various structures and will typically incorporate those found to be important for serotonin 5-HT2 receptor binding. Rings A and B are selected, according to embodiments of the invention, from benzene, pyridine, pyrimidine, pyrazine, pyridazine, pyrole, imidazole, triazole, pyrazole, thiophene, thiazole, furan and pyran. In a particular embodiment, ring A is selected from benzene and pyridine and ring B is selected from benzene, pyridine, pyrimidine, pyrazine, pyridazine, pyrole, imidazole, triazole, pyrazole, thiophene, thiazole, furan and pyran; and is particularly selected from benzene and pyridine. In specific embodiments of the invention, both rings A and B are benzene. It is to be appreciated that when rings A and B are heterocycles, the heteroatoms are shared with the central seven membered ring only when the shared heteroatom is N. Such tricycles are within the scope of the Formula I; one embodiment of which is described by Lednicer et al in *The Organic Chemistry of Drug Synthesis*, (1992, John Wiley & Sons Inc., New York) wherein ring B is imidazole that is fused to a thiazepine at one of the imidazole nitrogen atoms.

One or both rings A and B may be substituted with from 1 to 3, usually 1 or 2, substituents. When substituted, the substituents are selected from hydroxyl, halo, $C_{1-4}$alkyl, amino, nitro, cyano, halo-substituted $C_{1-4}$alkyl, $C_{1-4}$alkoxy, halo-substituted $C_{1-4}$alkoxy, $C_{1-4}$alkoxycarbonyl, $C_{1-4}$acyl, halo-substituted $C_{1-4}$acyl, cyclo-$C_{3-7}$alkyl, thio- $C_{1-4}$alkylene, $C_{1-4}$alkylthio, halo-substituted $C_{1-4}$alkylthio, cyanothio, tetrazolyl, N-piperidinyl, N-piperazinyl, N-morpholinyl, acetamido, $C_{1-4}$alkylsulfonyl, halosulfonyl, halo-substituted $C_{1-4}$alkylsulfonyl, $C_{1-4}$alkylsulfoxyl, sulfonamido, $C_{1-4}$alkylseleno, and $OSO_3H$.

Substitution sites on rings A and B will be limited in practice to the carbon atoms on the ring that are not shared with the central seven membered ring. For example, a benzene ring can accomodate up to 4 substituents; pyridine, and pyran, rings can accomodate up to 3 substituents; pyrimidine, pyrazine, pyridazine, pyrole, furan and thiophene rings can accomodate up to 2 substituents; imidazole, pyrazole and thiazole rings can accomodate only 1 substituent; and a triazole ring can accomodate no substituents. It is also to be understood that rings A and B may incorporate substituents at nitrogen atoms on the ring that are not shared with the central seven membered ring. For example the NH member of an imidazole ring may be substituted. In particular embodiments, rings A and B are substituted with from 1 to 2 substituents selected from chloro, fluoro, methyl, trifluoromethyl, methoxy, nitro, cyano and methylthio. In particularly preferred embodiments ring A is benzene substituted with 1 or 2 substituents selected from chloro, methyl, nitro and cyano and ring B is benzene substituted with 1 or 2 substituents selected from chloro, methoxy, trifluoromethyl and nitro.

In the central, 7-membered ring of the tricycle, $X_1$ may be any one of $CH_2$, O, NH, S, C=O, CH—OH, CH—N$(C_{1-4}$alkyl$)_2$, C=CHCl, C=CHCN, N—$C_{1-4}$alkyl, N-acetyl, $SO_2$ and SO, while $X_2$ - - - may be any one of N=, $CH_2$—, CH=, C(O)—, O—, and S—. In a particular embodiment of the invention, $X_1$ is O, S or NH. In another embodiment, $X_2$ - - - is N= or CH=. In a particularly preferred embodiment, $X_1$ is O, S or NH and $X_2$ - - - is N= or CH=. In specific embodiments $X_1$ and $X_2$ - - - are selected to form a seven membered ring selected from oxazepine, diazepine, thiazepine and thiepine. In preferred embodiments $X_1$ and $X_2$ - - - together with rings A and B are selected to form a tricycle that is selected from 5H-dibenzo[b,e][1,4]diazepine that is optionally choloro substituted, for example 7,8-dichloro; and dibenz[b,f][1,4]oxazepine that is optionally chloro substituted, for example 8-chloro.

In a particular embodiment of the invention, there are provided compounds of formula (I) that bind to muscarinic M1/M2 receptors, including:

11-(2-benzyl-2,5-diazabicyclo(2.2.1)hept-5-yl)-dibenz[b,f][1,4]oxazepine 8-chloro-11-(2-methyl-2,5-diazabicyclo(2.2.1)hept-5-yl)-dibenz[b,f][1,4]oxazepine; and 7,8-dichloro-11-(2-methyl-2,5-diazabicyclo(2.2.1)hept-5-yl)-dibenzo[b,e][1,4]diazepine.

In a more preferred embodiment, there are provided compounds of formula (I) that bind to muscarinic M1/M2 receptors in a selective manner relative to the serotonin 5-HT2 and dopamine D2 and D4 receptors, including:

8-chloro-11-(2-methyl-2,5-diazabicyclo(2.2.1)hept-5-yl)-dibenz[b,f][1,4]oxazepine; and 7,8-dichloro- 11-(2-methyl-2,5-diazabicyclo(2.2.1)hept-5-yl)-dibenzo[b,e][1,4]diazepine.

Acid addition salts of the compound of Formula I include for example those formed with inorganic acids e.g. hydrochloric, sulphuric or phosphoric acids and organic acids e.g. succinic, maleic, acetic or fumaric acid. Other non-pharmaceutically acceptable salts e.g. oxalates may be used for example in the isolation of compounds of Formula I for ligand use, or for subsequent conversion to a pharmaceutically acceptable acid addition salt. Also included within the scope of the invention are solvates and hydrates of the invention.

The conversion of a given compound salt to a desired compound salt is achieved by applying standard techniques, in which an aqueous solution of the given salt is treated with a solution of base e.g. sodium carbonate or potassium hydroxide, to liberate the free base which is then extracted into an appropriate solvent, such as ether. The free base is then separated from the aqueous portion, dried, and treated with the requisite acid to give the desired salt.

It will be appreciated that certain compounds of Formula I may contain an asymmetric centre. Such compounds will exist as two (or more) optical isomers (enantiomers). Both the pure enantiomers and the racemic mixtures (50% of each enantiomer), as well as unequal mixtures of the two, are included within the scope of the present invention. Further, all diastereomeric forms possible (pure enantiomers and mixtures thereof) are within the scope of the invention.

The compounds of the present invention can be prepared by processes analogous to those known in the art. The present invention therefore provides, in a further aspect, a process for the preparation of a compound of Formula I or a salt, solvate or hydrate thereof, which comprises the step of coupling a reagent of Formula A:

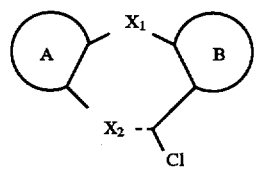  A with a reagent of Formula B:

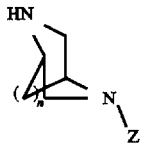  B in the presence of diisopropylethylamine (DIEA) or 1,8-diazabicyclo(5.4.0)-undec-7-ene (DBU) in acetonitrile.

The iminochloride, reagent (A), can be obtained commercially or can be synthesized using established techniques, for example, by treating the corresponding lactam (or ketone) (reagent Q) with $PCl_5$. Reagent Q may itself be commercially available or synthesized. For example, when $X_1$ is NH and $X_2$ - - - is N= (a diazepine), reagent (Q) may be prepared according to the procedures described by Giani et al (Synthesis, 1985, 550) by refluxing equimolar amounts of 2-chlorobenzoic acid, o-phenylenediamine and powdered copper in chlorobenzene. The following is a schematic representation of the reaction to obtain the diazepine form of reagent (Q):

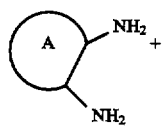

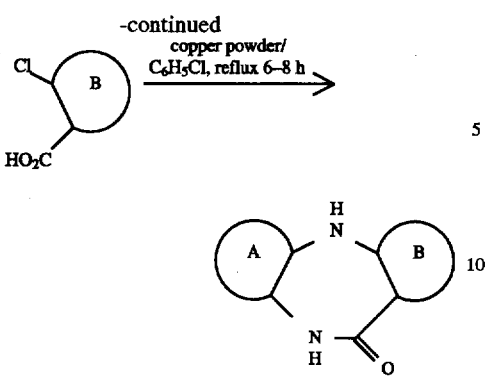

When $X_1$ is O and $X_2$ - - - is N= (an oxazepine), reagent (Q) may be prepared according to the procedures described by Klunder (J. Med. Chem. 1992, 35:1887) by condensation of a 2-aminophenol with 2-chloro-5-nitrobenzoyl chloride in THF to afford the corresponding carboxamide followed by refluxing with NaOH for ring closure. The following is a schematic representation of the steps to obtain the oxazepine form of reagent (Q):

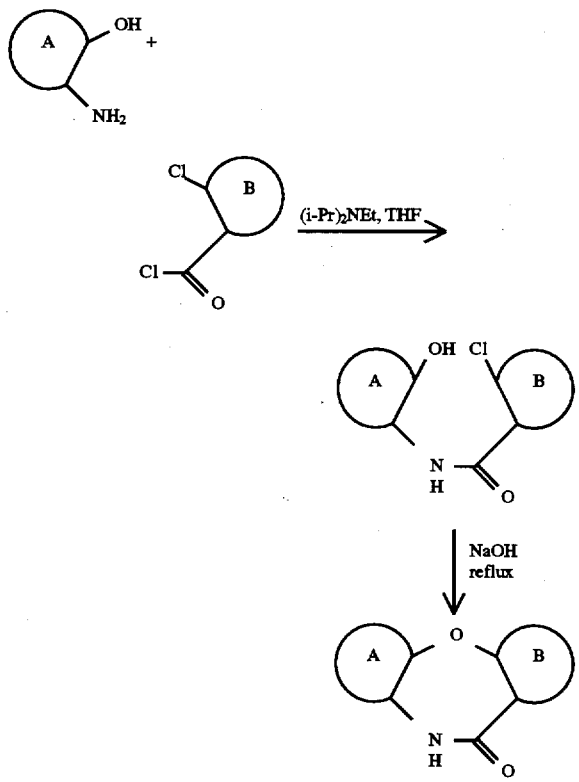

The thiepine form of reagent (Q), i.e. when $X_1$ is S and $X_2$ - - - is CH=, may be prepared according to the procedures described by Sindelar et al (Collect. Czech. Chem. Commun, 1983, 48(4):1187). When reagent (Q) is an oxepine i.e. when $X_1$ is O and $X_2$ - - - is $CH_2$—, it may be prepared in the manner reported by Harris et al (J. Med. Chem., 1982, 25(7):855); and the corresponding cycloheptene reagent (Q) i.e. when $X_1$ and $X_2$ - - - are both $CH_2$, may be prepared as reported by De Paulis et al (J. Med. Chem. 1981, 24(9):1021). The thiazepine reagent (Q) may be prepared in a four step process starting from 1-bromo-2-nitrobenzene and methyl thiosalicylate. The steps involve coupling; reduction of the nitro group; hydrolysis of the ester group; and finally ring closure.

Reagents of Formula B are commercially available or else can be synthesized using established synthetic techniques from starting materials that are commercially available.

In another embodiment of the invention, the compound is provided in labelled form, such as radiolabelled form e.g. labelled by incorporation within its structure of $^3H$ or $^{14}C$ or by conjugation to $^{125}I$. Such radiolabelled forms can be used to directly to distinguish muscarinic receptors from 5-HT2 and dopamine D4 and D2 receptors. This can be achieved by incubating preparations of the muscarinic receptor and the 5-HT2, D4 and D2 receptors with a radiolabelled muscarinic selective compound of the invention and then incubating the resulting preparation. The muscarinic, 5HT2 and dopamine receptors are then distinguished by determining the difference in membrane-bound radioactivity, with the muscarinic receptor exhibiting greater radioactivity, i.e. more radiolabelled compound bound. Furthermore, radiolabelled forms of the present compounds can be exploited to screen for more potent muscarinic ligands, by determining the ability of the test ligand to displace the radiolabelled compound of the present invention.

The binding profile of the present compounds indicates their utility as pharmaceuticals useful for the treatment of various conditions in which the use of a muscarinic receptor ligand is indicated, such as for the treatment of anxiety and schizophrenia.

For use in medicine, the compounds of the present invention are usually administered in a standard pharmaceutical composition. The present invention therefore provides, in a further aspect, pharmaceutical compositions comprising an effective amount of a compound of Formula I or a pharmaceutically acceptable salt, solvate or hydrate thereof and a pharmaceutically acceptable carrier.

The compounds of the present invention may be administered by a convenient route, for example by oral, parenteral, buccal, sublingual, nasal, rectal or transdermal administration and the pharmaceutical compositions formulated accordingly.

The compounds and their pharmaceutically acceptable salts which are active when given orally can be formulated as liquids, for example syrups, suspensions or emulsions, tablets, capsules and lozenges.

A liquid formulation will generally consist of a suspension or solution of the compound or pharmaceutically acceptable salt in a suitable pharmaceutical liquid carrier for example, ethanol, glycerine, non-aqueous solvent, for example polyethylene glycol, oils, or water with a suspending agent, preservative, flavouring or colouring agent.

A composition in the form of a tablet can be prepared using any suitable pharmaceutical carrier routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into hard gelatin capsule; alternatively, a dispersion or suspension can be prepared using any suitable pharmaceutical carrier, for example aqueous gums, celluloses, silicates or oils and the dispersion or suspension filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilized and then reconstituted with a suitable solvent just prior to administration.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as flurochlorohydrocarbon. The aerosol dosage forms can also take the form of a pump-atomizer.

Compositions suitable for buccal or sublingual administration include tablets, lozenges, and pastilles, wherein the active ingredient is formulated with a carrier such as sugar, acacia, tragacanth, or gelatin and glycerine.

Compositions for rectal administration are conveniently in the form of suppositories containing a conventional suppository base such as cocoa butter.

Preferably, the composition is in unit dose form such as a tablet, capsule or ampoule. Suitable unit doses i.e. therapeutically effective amounts; can be determined during clinical trials designed appropriately for each of the conditions for which administration of a chosen compound is indicated and will of course vary depending on the desired clinical endpoint. It is anticipated that dosage sizes appropriate for administering the compounds of the examples will be in the range from about 0.1 to about 500 mg/kg body weight eg. 0.1 to about 100 mg/kg body weight, and will be administered in a frequency appropriate for initial and maintenance treatments.

EXAMPLE 1

Preparation of intermediate (1S,4S)-2-Methyl-2,5-diazabicyclo(2.2.1)heptane (1S,4S)-2-Benzyl-2,5-diazabicyclo(2.2.1)heptane dihydrobromide (Medinger & Söhne Sanochemica-Gruppe, Austria, M-P701, 5.0 g, 0.0143 mol) was stirred for 10 min in a solution of 1N KOH (0.029 mol). The liberated base was extracted with $CHCl_3$; dried ($K_2CO_3$) and evaporated to dryness in vacuo; yield 2.4 g, (88%).

EXAMPLE 2

Preparation of intermediate (1S,4S)-5-methyl-2,5-diazabicyclo(2.2.1)heptane

To a solution of (1S,4S)-2-Benzyl-2,5-diazabicyclo(2.2.1) heptane (2.4 g, 0.013 mol) in dry $CH_2Cl_2$, triethylamine (8.7 mL, 0.063 mol) was added and upon cooling of the solution to 0° C. ethyl chloroformate (1.8 mL, 0.019 mol) was added. The mixture was warmed to room temperature and mixed for 2 hrs. The reaction mixture was diluted with ice cold water (30 mL) and extracted with $CH_2Cl_2$. The combined organic phases were dried ($K_2CO_3$) and concentrated in vacuo. The product (1S,2S)-2-benzyl-5-ethoxycarbonyl-2,5-diazabicyclo(2.2.1)heptane was dried in a desiccator over $K_2CO_3$.

To a solution of (1S,4S)-2-benzyl-5-ethoxycarbonyl-2,5-diazabicyclo(2.2.1)heptane (3.3 g, 0.013 mol) in THF at −10° C., was added dropwise 1M $LiAlH_4$ in ether (26.3 mL, 0.026 mol). The reaction mixture was slowly warmed to room temperature and mixed overnight. Upon cooling to 0° C., 4 mL of 95% THF:$H_2O$ was slowly added followed by 4 mL of $H_2O$. The mixture was diluted with $NH_4OH$ (40 mL), filtered through a celite pad and concentrated in vacuo. The remaining $NH_4OH$ solution was further diluted with $NH_4OH$ (15 mL) and extracted with $CH_2Cl_2$. The combined organic phases were dried ($K_2CO_3$) and concentrated in vacuo to yield (1S,4S)-2-benzyl-5-methyl-2,5diazabicyclo (2.2.1)heptane (2.2 g, 86%).

To a solution of (1S,4S)-2-benzyl-5-methyl-2, 5diazabicyclo(2.2.1)heptane (2.2 g, 0.011 mol) in methanol, was added $Pd(OH)_2$ (20% w/w) and the mixture was stirred overnight under $H_2$. The reaction mixture was filtered through a celite pad and concentrated in vacuo. The product (1S,4S)-5-methyl-2,5-diazabicyclo(2.2.1)heptane, an oil was stored with KOH pellets under argon at −20° C. in the dark; yield 1.2 g, (98%).

EXAMPLE 3

Preparation of intermediate 8-chloro- 11-oxo-dibenz[b,f][1,4]thiazepine

A solution of NaH (1.1 g, 0.04 mol) in dry THF (20 mL) was cooled to 0° C. To this mixture methyl thiosalicylate (5.1 mL, 0.036 mol) was added dropwise via syringe. The reaction mixture was warmed to room temperature to ensure completion of the reaction. The solution was cooled to 0° C. and 2,5-dichloronitrobenzene (7.0 g, 0.036 mol) was added dropwise in THF (20 mL). The reaction was stirred at 0° C. for 30 min then stirred at room temperature for 4 hrs. The reaction was quenched with 5mL ice cold water and then diluted with EtOAc (300 mL). The phases were separated and the organic phase was washed with sat. $NaHCO_3$, water and brine. The organic phase was dried ($MgSO_4$) and concentrated in vacuo. Recrystallization was done in $CHCl_3$ and $Et_2O$; to yield 2-nitro-4-chloro-2'-methoxycarbonyl*diphenylsulfide 10.9 g, (93%).

To a solution of 2-nitro-4-chloro-2'-methoxycarbonyl-diphenylsulfide (10.3 g, 0.032 mol) in 78% ethanol (200 mL) a solution of $CaCl_2$ (2.3 g, 0.019 mol) in 4 mL water was added. Zn dust (68.9 g, 1.05 mol) was added and the mixture was refluxed for 3 hrs. The hot mixture was filtered through a celite pad and washed with hot ethanol. The filtrate was concentrated in vacuo to obtain the solid 2-amino-4-chloro-2'-methoxycarbonyl-diphenylsulfide; yield 10.01 g, (98%).

To a solution of 2-amino-4-chloro-2'-methoxycarbonyl-diphenylsulfide (9.4 g, 0.032 mol) in ethanol, was added 1N KOH (67 mL, 0.067 mol) and the mixture refluxed for 2 hrs. The ethanol was removed and the solution was cooled to 0° C. The product 2-amino-4-chloro-2'-carboxyl-diphenylsulfide was precipitated by dropwise addition of conc. HCl to pH3. The precipitate was filtered and collected and dried; yield 8.5 g, (95%).

To a solution of 2-amino-4-chloro-2'-carboxyl-diphenylsulfide (8.4 g, 0.03 mol) in dry $CH_2Cl_2$, was added 4-dimethylaminopyridine (1.2 g, 0.009 mol) and 1-(3-dimethylaminopropyl)-3-ethylcarbodiimide hydrochloride (10. g, 0.053 mol) and stirred at room temperature overnight. The solution was concentrated in vacuo, then diluted with water (200 mL) and ether (50 mL) and placed in refrigerator. The precipitate 8-chloro-11-oxo-dibenz[b,f][1,4]thiazepine was filtered and dried under vacuum; yield 7.2 g, (92%).

In a like manner, the intermediate 11-oxo-dibenz[b,f][1,4]thiazepine was prepared starting from 1-bromo-2-nitrobenzene

EXAMPLE 4

Preparation of 8-chloro-11-(2-methyl-2,5-diazabicyclo (2.2.1)hept-5-yl)-dibenzo[b,f][1,4]thiazepine To a solution of 8-chloro-11-oxo-dibenz[b,f][1,4] thiazepine (0.3 g, 0.0011 mol) in dry toluene (10 mL), was added $PCl_5$ (0.27 g, 0.0013 mol) in one portion and then refluxed for 4 hrs. The toluene was removed in vacuo and the imino chloride was dried under vacuum.

To a solution of imino chloride (0.32 g, 0.0011 mol) in dry acetonitrile (20 mL), was added diisopropylethylamine (1.12 mL, 0.006 mol) and (1S,2S)-2-methyl-2,5-diazabicyclo(2.2.1)heptane (0.36 g, 0.003 mol) via syringe. The mixture was refluxed for 6 hrs. The acetonitrile was evaporated off in vacuo and the resulting oil was diluted in water and extracted with $CH_2Cl_2$. To the resulting $CH_2Cl_2$ phase 1N HCl (20 mL) was added. The aqueous phase was washed with $CH_2Cl_2$, basified with $NH_4OH$ to pH 9-10 and extracted with $CH_2Cl_2$. The resulting organic phase was dried ($MgSO_4$) and concentrated in vacuo. The crude material was chromatographed ($CHCl_3$:MeOH, 95:5) to give 8-chloro-11-(2-methyl-2,5-diazabicyclo(2.2.1)hept-5-yl) dibenzo[b,f][1,4]thiazepine (0.26 g, 65%, mp 62°–64° C.).

In a like manner the following compounds were prepared:
a) 11-(2-methyl-2,5-diazabicyclo(2.2.1)hept-5-yl)-dibenzo [b,f][1,4]thiazepine (yield 40%, mp 60°–61° C.) from 11-oxo-dibenzo[b,f][1,4]thiazepine;
b) 8-chloro-11-(2-methyl-2,5-diazabicyclo(2.2.1)hept-5-yl)-dibenz[b,f][1,4]oxazepine (yield 53%, mp 58°–60° C.) from 8-chloro-11-oxo-dibenz[b,f][1,4]oxazepine prepared according to the procedures described by Coyne et al, in J. Med. Chem., 1967, 10:541. Briefly, this entailed coupling potassium salicylaldehyde with 2,5-dichloronitrobenzene, followed by oxidation to carboxylic acid, reduction of nitro, and finally ring closure, to yield the desired 8-chloro compound (m.p. 256°–258° C.); and

EXAMPLE 5

Preparation of 11-(2-benzyl-2,5-diazabicyclo(2.2.1)hept-5-yl)-dibenz[b,f][1,4]oxazepine To a solution of 11-oxo-dibenz[b,f][1,4]oxazepine (Aldrich) (0.149 g, 0.0007 mol) in dry toluene (10 mL), was added (1S,4S)-2-benzyl-2,5-diazabicyclo(2.2.1)heptane (0.54 g, 0.003 mol) and $TiCl_4$ (0.75 mL, 0.0008 mol) via syringe. The mixture was stirred at room temperature for 30 min then refluxed for 5 hrs. The reaction mixture was cooled and dumped into conc. $NH_4OH$ and extracted with $CHCl_3$. The combined organic phases were dried ($MgSO_4$) and concentrated in vacuo. The crude material was chromatographed (hexane:EtOAc, 1:1) to give 11-(2-benzyl-2,5-diazabicyclo(2.2.1) hept-5-yl)-dibenz[b,f][1,4]oxazepine (yield 0.131 g, mp 70°–72° C.).

In a like manner 7,8-dichloro-11-(2-methyl-2,5-diazabicyclo(2.2.1)hept-5-yl)-dibenzo [b,e][1,4]diazepine (yield 10%, mp 70°–72° C.) was prepared from 7,8-chloro-11-oxo-dibenzo[b,e][1,4]diazepine which was prepared according to the procedures described by Giani et al, in Synthesis 550, (1985).

EXAMPLE 6

Muscarinic Receptor Binding Assay

M1/M2 receptor-binding affinities of the compounds of examples 4 and 5 were evaluated according to their ability to reduce binding of tritiated RS (±) quinuclidinyl benzylate ($^3$H-QNB), a muscarinic receptor antagonist. The potency of the test compound to reduce 3H-QNB binding directly is correlated to its binding affinity for the receptor.

M1/M2 Receptor Preparation

Rat frontal cortex tissue was initially prepared by Analytical Biological Services by the following steps: homogenizing in 10 volumes of 0.32M sucrose at 4° C.; centrifuging at 900× g for 10 minutes; centrifuging supernatant at 48,000× g for 20 minutes; suspending pellet in 20 volumes 50 mM Tris HCl, pH 7.7 containing 5 mM calcium chloride; incubating at 37° C. for 30 minutes; centrifuging at 48,000× g for 30 minutes; suspending pellets in 2 volumes of buffer and storing in 15 mL aliquots at −70° C. On day of study, the tissues were thawed on ice for 20 minutes. The tissues were pooled together and resuspended in 30 mL incubation buffer (40.5 mM $Na_2HPO_4$, 9.5 mM $KH_2PO_4$, 50 μM ascorbic acid) pH 7.4 at 4° C. The tissues were then homogenized with a Kinematica CH-6010 Kriens-LU homogenizer for 15 seconds, setting 6. The homogenate was centrifuged at 20,000 rpm for 30 minutes at 4° C., Beckman SW28 rotor. The entire pellet was resuspended in 10 mL of incubation buffer (40.5 mM $Na_2HPO_4$, 9.5 mM $KH_2PO_4$, 50 μM ascorbic acid, pH 7.4) and homogenized with a cold Douce homogenizer, 10 strokes, 10 mL buffer, at 4° C. The protein concentration was determined using the Pierce BCA Assay, adding 10 μL of membrane preparation per sample, in triplicate. Membrane preparations were made in incubation buffer.

Total $^3$H-QNB Binding

The incubation was started in 12×75 mm borosilicate glass tubes by the addition of 1000 μL membrane homogenate (100 μg protein) to a solution 800 μL incubation buffer (40.5 μM $Na_2HPO_4$, 9.5 mM $KH_2PO_4$, 50 μM ascorbic acid, pH 7.4) and 200 μL $^3$H-QNB (0.126 nM final concentration, 86 Ci/mmol, NEN Research Products). The tubes were vortexed and placed in a 32° C. water bath for 60 minutes. The binding reaction was stopped by immersing the tubes in an ice water bath for 5 minutes. The samples were then filtered under vacuum over glass fibre (Whatman GF/B) soaked in 0.3% polyethylenimine (PEI) in 40.5 mM $Na_2PO_4$, 9.5 mM $KH_2PO_4$ buffer (pH 7.4) for at least 2 hours and then washed 3 times with 5 mL ice cold 40.5 mM $Na_2HPO_4$, 9.5 mM $KH_2PO_4$ buffer (pH 7.4) using a Brandell Cell Harvester. Individual filter disks were put in scintillation vials (Biovials, Beckman). Ready Protein Plus liquid scintillant (5 mL, Beckman) was added and the vials counted by liquid scintillation spectrophotometry (Beckman LSC 6500) after equilibrating for three hours at room temperature to give total binding ($B_T$).

Non-Specific Binding

The incubation was started in 12×75 mm borosilicate glass tubes by the addition of 1000 μL membrane homogenate (100 μg protein) to a solution of 800 μL (1 μM final conc.) atropine sulphate (1 mM stock dissolved in water, diluted in incubation buffer, Research Biochemicals), and 200 μL $^3$H-QNB (0.126 nM final concentration, 86 Ci/mmol, NEN Research Products). The tubes were vortexed and placed in a 32° C . water bath for 60 minutes. The binding reaction was stopped by immersing the tubes in an ice water bath for 5 minutes. The samples were then filtered and counted using the same procedure as in the total binding assay described above to give the non-specific binding value (NSB).

Displacement Binding

The incubation was started in 12×75 mm borosilicate glass tubes by the addition of 1000 μL membrane homogenate (100 μg protein) to a solution of 800 μL test compound (1 mM stock dissolved in DMSO, stored at −20° C. in polypropylene cryogenic storage vials and diluted in incubation buffer), and 200 μL $^3$H-QNB (0.126 nM final concentration, 86 Ci/mmol, NEN Research Products). The tubes were vortexed and placed in a 32° C. water bath for 60 minutes. The binding reaction was stopped by immersing the tubes in an ice water bath for 5 minutes. The samples were then filtered and counted using the same procedure as in the total binding assay described above to give the displacement binding value ($B_D$).

Calculations

The test compounds were initially assayed at 1 and 0.1 µM and then at a range of concentrations chosen such that the middle dose would cause about 50% inhibition of $^3$H-QNB binding. Specific binding in the absence of test compound ($B_o$) was the difference of total binding ($B_T$) minus non-specific binding (NSB) and similarly specific binding (in the presence of test compound) (B) was the difference of displacement binding ($B_D$) minus non-specific binding (NSB). IC$_{50}$ was determined from an inhibition response curve, logit-log plot of % B/B$_o$ vs concentration of test compound.

Ki was calculated by the Cheng and Prustoff transformation:

$$Ki=IC_{50}/(1+[L]/K_D)$$

where [L] is the concentration of $^3$H-QNB used in the assay and $K_D$ is the dissociation constant of $^3$H-QNB determined independently under the same binding conditions.

EXAMPLE 7

5-HT2 Receptor Binding Assay

5-HT2 receptor-binding affinities of the compounds of examples 4 and 5 were evaluated according to their ability to reduce binding of tritiated ketanserin, a serotonin receptor antagonist. The potency of the test compound to reduce $^3$H-ketanserin binding is directly correlated to its binding affinity for the receptor.

5-HT2 Receptor Preparation

Rat frontal cortex tissue was initially prepared by Analytical Biological Services by the following steps: homogenizing in 10 volumes of 0.32M sucrose at 4° C.; centrifuging at 900× g for 10 minutes; centrifuging supernatant at 48,000× g for 20 minutes; suspending pellet in 20 volumes 50 mM Tris HCl, pH 7.7 containing 5 mM calcium chloride; incubating at 37° C. for 30 minutes; centrifuging at 48,000× g for 30 minutes; suspending pellets in 2 volumes of buffer and storing in 15 mL aliquots at −70° C. On day of study, tissues were thawed on ice for 20 minutes. The entire pellet was resuspended in 5 mL of buffer (50 mM Tris, 0.5 mM EDTA, 10 mM MgSO$_4$, 10 µM pargyline, 0.1% ascorbic acid, pH 7.4) at 4° C. and sonicated with a Sonifier Cell Disrupter 350 at 8 microtip units for 6 seconds power 80. The protein concentration was determined using the Pierce BCA Assay, adding 1 µL of membrane preparation per sample, in triplicate. Membrane preparations were made in incubation buffer.

Total $^3$H-ketanserin Binding

The incubation was started in 12×75 mm polypropylene glass tubes by the addition of 400 µL membrane preparation (100 µg protein) to a solution of 500 µL incubation buffer (50 mM Tris, 0.5 mM EDTA, 10 mM MgSO$_4$, 10 µM pargyline, 0. 1% ascorbic acid, pH 7.4) and 100 µL $^3$H-ketanserin (1 nM final concentration, 85 Ci/mmol, NEN Research Products). The tubes were vortexed and incubated at room temperature for 30 minutes. The binding reaction was stopped by filtering. The samples were filtered under vacuum over glass fibre filters (Whatman GF/B) soaked in 0.3% polyethylenimine (PEI) in 50 mM Tris (pH 7.4) for 2 hours and then washed 3 times with 5 mL ice cold 50 mM Tris buffer (pH 7.4) using a Brandell Cell Harvester. Individual filter disks were put in scintilation vials (Biovials, Beckman). Ready Protein Plus liquid scintilant (5 mL, from Beckman) was added and the vials were counted by liquid scintillation spectrophotometry (Beckman LSC 6500) after equilibrating for three hours at room temperature to give total bidning ($B_T$).

Non-Specific Binding

The incubation was started in 12×75 mm polypropylene tubes by the addition of 400 µL membrane preparation (100 µg protein) to a solution of 500 µL methysergide (30 µM final conc. from 1 mM stock dissolved in DMSO and diluted in incubation buffer, Research Biochemicals Inc.) and 100 µL $^3$H-ketanserin (1 nM final concentration, 85 Ci/mmol, NEN Research Products). The tubes were vortexed and incubated at room temperature for 30 minutes. The binding reaction was stopped by filtering. The filters were washed and counted using the same procedure as in the total binding assay described above to give the non-specific binding value (NSB).

Displacement Binding

The incubation was started in 12×75 mm polypropylene tubes by the addition of 400 µL membrane preparation (100 µg protein) to a solution of 500 µL test compound (initially 1 and 0. 1M final conc. in incubation buffer) and 100 µL $^3$H-ketanserin (1 nM final concentration, 85 Ci/mmol, NEN Research Products). The tubes were vortexed and incubated at room temperature for 30 minutes. The binding reaction was stopped by filtering. The filters were washed and counted using the same procedure as in the total binding assay described above to give the displacement binding value ($B_D$).

Calculations

The test compounds were initially assayed at 1 and 0.1 µM and then at a range of concentrations chosen such that the middle dose would cause about 50% inhibition of $^3$H-ketanserin binding. Specific binding in the absence of test compound ($B_o$) was the difference of total binding ($B_T$) minus non-specific binding (NSB) and similarly specific binding (in the presence of test compound) (B) was the difference of displacement binding ($B_D$) minus non-specific binding (NSB). IC$_{50}$ was determined from an inhibition response curve, logit-log plot of % B/B$_o$ vs concentration of test compound.

Ki was calculated by the Cheng and Prustoff transformation:

$$Ki=IC_{50}/(1+[L]/K_D)$$

where [L] is the concentration of $^3$H-ketanserin used in the assay and $K_D$ is the dissociation constant of $^3$H-ketanserin determined independently under the same binding conditions.

EXAMPLE 8

Dopamine Receptor Binding Assay

D2 and D4 receptor-binding affinities of the compounds of examples 1 and 2 were evaluated according to their ability to reduce binding of $^3$H-spiperone as compared to the reference compound clozapine. The potency of the test compound to reduce $^3$H-spiperone binding directly correlated to its binding affinity for the receptor.

D4 Receptor Preparation

HEK 298 (human embryonic kidney) cells stably transfected with human D4 receptor (D4.2 sub-type) were grown in NUNC cell factories for 5 days (75% confluency) without a media change and removed with versene (approximately 19 mg of cells per cell factory tray). The cells were then centrifuged in a Sorval centrifuge for 10 minutes, 5000 rpm (GS3 rotor) and the pellets quickly frozen in liquid nitrogen and stored at −80° C. until used in binding assay. When used in the assay, cells were thawed on ice for 20 minutes and then 10 mL of incubation buffer (50 mM Tris, 1 mM EDTA, 4 mM $MgCl_2$, 5 mM KCl, 1.5 mM $CaCl_2$, 120 mM NaCl, pH7.4) was added. The cells were then vortexed to resuspend pellet and homogenized with a Kinematica CH-6010 Kriens-LU homogenizer for 15 seconds at setting 7. Concentration of receptor protein was determined using the Pierce BCA assay.

D2 Receptor Preparation $GH_4C_1$ (rat pituitary) cells stably transfected with the human D2 receptor (short isoform) were grown in $CO_2$ independent media in roller bottles (1500 $cm^2$) for 10 days. 100 μM $ZnSO_4$ was added to the cells (the D2 promoter being zinc inducible). After 16 hours, fresh media was added to allow the cells to recover for 24 hours. The cells were harvested using versene and then centrifuged in a Sorval centrifuge for 10 minutes, at 5000 rpm (GS3 rotor). Pellets were quickly frozen in liquid nitrogen and stored at −80° C. until used in the binding assays. When used in the assay, cells were thawed on ice for 20 minutes. Each roller bottle produced approximately 72 mg of protein. 10 mL of incubation buffer was added to the pellets which were then vortexed, resuspended and homogenized with a Kinematica CH-6010 Kriens-LU homogenizer for 15 seconds at setting 7. The receptor protein concentration was determined using the Pierce BCA assay.

Total Spiperone Binding Assay

The incubation was started by the addition of 500 μl (50 μg protein) membrane homogenate to a solution of 900 μl incubation buffer and 100 μl (0.25 nM final conc.) $^3$H-spiperone (90 Ci/mmol Amersham diluted in borosilicate glass vial) in 12×75 mm polypropylene tubes. The tubes were vortexed and incubated at room temperature for 90 minutes. The binding reaction was stopped by filtering using a Brandell Cell Harvester. The samples were filtered under vacuum over glass fibre filters (Whatman GF/B) presoaked for 2 hours in 0.3% polyethylenimine (PEI) in 50 mM Tris buffer (pH7.4). The filters were then washed 3 times with 5 mL ice cold 50 mM Tris buffer (pH7.4). Individual filter disks were put in scintillation vials (Biovials, Bechman). Ready Protein Plus liquid scintillant (5 mL, Beckman) was added and the vials counted by liquid scintillation spectrophotometry (Beckman LSC 6500) after equilibrating for three hours at room temperature to determine total binding ($B_T$).

Non-Specific Binding Assay for D4

The incubation was started by the addition of 500 μl (50 μg protein) membrane homogenate to a solution of 400 μl incubation buffer, 100 μl $^3$H-spiperone (90 Ci/mmol Amersham diluted in borosilicate glass vial to 0.25 nM final conc.) and 500 μl (30 μM final conc.) of fresh dopamine (Research Biochemicals Inc., light protected and dissolved in incubation buffer) in 12×75 mm polypropylene tubes. The tubes were vortexed and incubated at room temperature for 90 minutes at which time the binding reaction was stopped by filtering. The filters were washed and counted using the same procedure as in the total binding assay described above to give the non-specific binding value (NSB).

Non-Specific Binding Assay for D2

This assay employed the same procedures as the non-specific binding assay for D4 with the exception that 2 μM (final conc.) of (−) sulpiride (Research Chemicals Inc.) was used in place of dopamine.

Displacement Binding Assay

The incubation was started by the addition to 12×75 mm polypropylene tubes 500 μl (50 μg protein) membrane homogenate to a solution of 400 μl incubation buffer, 100 μl (0.25 final conc.) $^3$H-spiperone (90Ci/mmol, Amersham, diluted in borosilicate glass vial to) and 500 μl of test compound that was prepared from 1 mM stock dissolved in DMSO and stored at −20° C. in polypropylene cryogenic storage vials until dilution in incubation buffer in borosilicate glass vials. The tubes were vortexed and incubated at room temperature for 90 minutes at which time the binding reaction was stopped by filtering. The filters were washed and counted using the same procedure as in the total binding assay described above to give the displacement binding value ($B_D$).

Calculations

The test compounds were initially assayed at 1 and 0.1 μM and then at a range of concentrations chosen such that the middle dose would cause about 50% inhibition of $^3$H-spiperone binding. Specific binding in the absence of test compound ($B_o$) was the difference of total binding ($B_T$) minus non-specific binding (NSB) and similarly specific binding (in the presence of test compound) (B) was the difference of displacement binding ($B_D$) minus non-specific binding (NSB). $IC_{50}$ was determined from an inhibition response curve, logit-log plot of % $B/B_o$ vs concentration of test compound.

Ki was calculated by the Cheng and Prustoff transformation:

$$Ki=IC_{50}/(1+[L]/K_D)$$

where [L] is the concentration of $^3$H-spiperone used in the assay and $K_D$ is the dissociation constant of $^3$H-spiperone determined independently under the same binding conditions.

Assay results are reported in the following Table:

| RECEPTOR AFFINITIES (Ki in nM) | | | | | |
|---|---|---|---|---|---|
| COMPOUND | STRUCTURE | M1/M2 | D4 | D2 | 5-HT2 |
| clozapine | 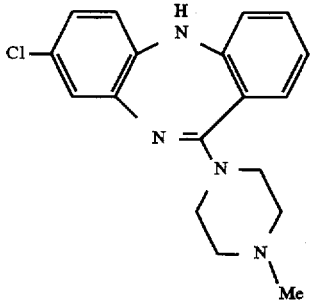 | 16 | 23 | 230 | 7.5 |
| 11-(2-benzyl-2,5-diazabicyclo(2.2.1)hept-5-yl)-dibenz[b,f][1,4]oxazepine | 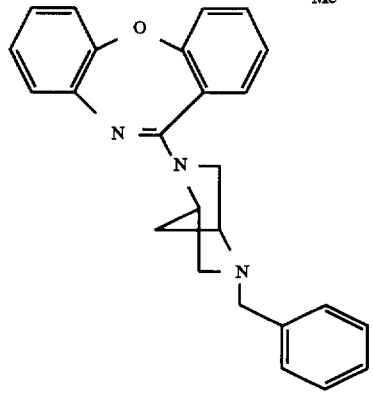 | 882 | 632 | 1333 | 3667 |
| 8-chloro-11-(2-methyl-2,5-diazabicyclo(2.2.1)hept-5-yl)-dibenz[b,f][1,4]oxazepine | 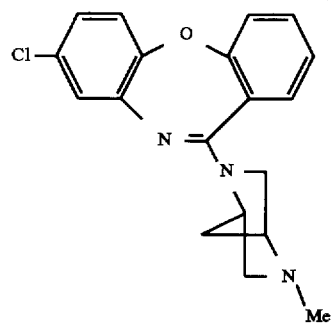 | 28 | 4769 | 4518 | 1019 |
| 7,8-dichloro-11-(2-methyl-2,5-diazabicyclo(2.2.1)hept-5-yl)-dibenzo[b,e][1,4]diazepine | 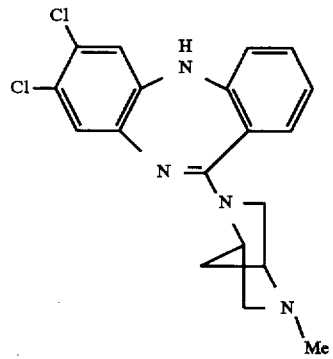 | 41 | 4769 | 4711 | 1600 |

We claim:
1. A compound of Formula I:

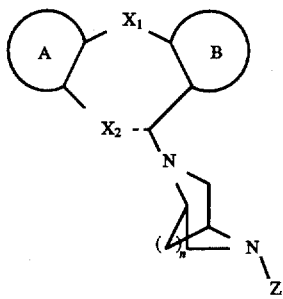

wherein:
A and B are independently selected from substituted or unsubstituted benzene,
$X_1$ is selected from O, S, $SO_2$ and SO;
$X_2$ - - - is selected from $CH_2$—, CH=, and C(O)—,
n is 1 or 2; and
Z is selected from $C_{1-6}$alkyl unsubstituted or substituted with a substituent selected from OH, halo, $C_{1-4}$alkyl and C alkoxy;
and acid addition salts, solvates and hydrates thereof.

2. The compound according to claim 1, wherein A and B are independently unsubstituted or substituted with 1 or 2 substituents selected independently from hydroxyl, halo $C_{1-4}$alkyl, amino, nitro, cyano, halo-substituted $C_{1-4}$alkyl, $C_{1-4}$alkoxy, halo-substituted $C_{1-4}$alkoxy, $C_{1-4}$alkoxycarbonyl, $C_{1-4}$acyl, cyclo-$C_{1-7}$alkyl, thio-$C_{1-4}$alkylene, $C_{1-4}$alkylthio, halo-substituted $C_{1-4}$alkylthio, cyanothio, tetrazolyl, N-piperidinyl, N-piperazinyl, N-morpholinyl, acetamido, $C_{1-4}$alkylsulfonyl, halosulfonyl, halo-substituted $C_{1-4}$alkylsulfonyl, $C_{1-4}$alkysulfoxyl, sulfonamido, $C_{1-4}$alkylseleno, and $OSO_3H$.

3. The compound according to claim 2, wherein rings A and B are both benzene optionally substituted with 1 or 2 substituents selected independently from hydroxyl, halo $C_{1-4}$alkyl, amino, nitro, cyano, halo-substituted $C_{1-4}$alkyl, $C_{1-4}$alkoxy, halo-substituted $C_{1-4}$alkoxy, $C_{1-4}$alkoxycarbonyl, $C_{1-4}$acyl, cyclo-$C_{1-7}$alkyl, thio-$C_{1-4}$alkylene, $C_{1-4}$alkylthio, halo-substituted $C_{1-4}$alkylthio, cyanothio, tetrazolyl, N-piperidinyl, N-piperazinyl, N-morpholinyl, acetamido, $C_{1-4}$alkylsulfonyl, halosulfonyl, halo-substituted $C_{1-4}$alkylsulfonyl, $C_{1-4}$alkysulfoxyl, sulfonamido, $C_{1-4}$alkylseleno, and $OSO_3H$.

4. The compound according to claim 1, wherein A is benzene which is unsubstituted or substituted by 1 or 2 chloro substituents.

5. The compound according to claim 1, wherein $X_1$ is O.

6. The compound according to claim 1, wherein Z is methyl and n is 1.

7. The compound according to claim 2, wherein Z is methyl and n is 1.

8. The compound according to claim 4, wherein Z is methyl and n is 1.

9. A pharmaceutical composition, comprising a therapeutically effective amount of a compound according to claim 1, and a pharmaceutically acceptable carrier.

* * * * *